United States Patent [19]

Rogier

[11] 4,339,389

[45] Jul. 13, 1982

[54] POLYGLYCIDYL ETHERS

[75] Inventor: Edgar R. Rogier, Minnetonka, Minn.

[73] Assignee: Henkel Corporation, Minneapolis, Minn.

[21] Appl. No.: 81,950

[22] Filed: Oct. 4, 1979

[51] Int. Cl.³ .................. C07D 303/27; C07D 303/26
[52] U.S. Cl. ...................................... 549/555; 528/87; 528/418; 528/419
[58] Field of Search .................................... 260/348.64

[56] References Cited

U.S. PATENT DOCUMENTS

| | | | |
|---|---|---|---|
| 2,581,464 | 1/1952 | Zech | 260/348.64 |
| 2,599,468 | 6/1952 | McKeever | 252/56 R |
| 2,809,186 | 10/1957 | Smith et al. | 260/348.6 |
| 3,117,138 | 1/1964 | Price | 260/348.6 |
| 3,243,414 | 3/1966 | DeWitt et al. | 260/18 TN |

OTHER PUBLICATIONS

A. M. Paquin, Epoxydverbindungen und Epoxydharze (1958) pp. 166–168, 246.

*Primary Examiner*—Norma S. Milestone
*Attorney, Agent, or Firm*—Forrest L. Collins; Patrick J. Span

[57] ABSTRACT

The present invention describes the production of high molecular weight polyglycidyl ethers.

4 Claims, No Drawings

POLYGLYCIDYL ETHERS

CROSS-REFERENCE TO RELATED APPLICATION

Related subject matter is disclosed in applicant's prior application Ser. No. 26,858, filed Apr. 4, 1979 and now U.S. Pat. No. 4,216,343, issued Aug. 5, 1980.

BACKGROUND OF THE INVENTION

1. Field of the Invention

This invention relates to products and processes useful in the manufacture of synthetic resins from polyglycidyl materials.

2. Description of the Art Practice

The products of the present invention are obtained from raw materials subjected to hydroformylation. Hydroformylation is basically defined as the addition of a formyl group through the reaction of an unsaturated compound with carbon monoxide and hydrogen. The basic technology for the manufacture of hydroformylated products and consequently their derivatives is amply set out hereinafter.

In the past several attempts have been made to prepare hydroformylated products or similar materials such as is described in U.S. Pat. No. 2,437,600 to Gresham et al issued Mar. 9, 1948. The Gresham patent relates to the synthesis of organic oxygen containing compounds, in particular aldehydes. U.S. Pat. No. 2,533,276 to McKeever et al issued Dec. 12, 1950 describes ester-acetals obtained with cobalt catalysts. U.S. Pat. No. 2,599,468 to McKeever issued June 3, 1952 describes the process of preparing nonadecyl glycols.

U.S. Pat. No. 3,040,090 issued June 19, 1962 to Alderson et al discusses the reaction of hydrocarbons with aldehydes and higher alcohols in methanol to prepare organic oxy compounds. The Alderson et al patent sets forth a number of metallic catalysts which may be employed in effecting the reactions described therein.

In U.S. Pat. No. 3,043,871 issued July 10, 1962 to Buchner et al the production of heptadecane-dicarboxylic acid is described. Foreman et al in U.S. Pat. No. 3,227,640 issued Jan. 4, 1966 describes the production of olefinically unsaturated alcohols which are of use in manufacturing some of the end products of the present invention. Bernardy et al describe oxyalkylated dimethylol and trimethylol alkanes in U.S. Pat. No. 3,290,387 issued Dec. 6, 1966. U.S. Pat. No. 3,420,898 issued to Van Winkle et al on Jan. 7, 1969 discusses the use of cobalt complexes with certain phosphine compounds in the production of primary alcohols with carbon monoxide and hydrogen.

U.S. Pat. No. 3,530,190 issued Sept. 22, 1970 to Olivier discusses hydrocarbonylation of olefins using certain metal salts. The foregoing reference also discusses the recovery of the complexed metal catalyst. In a patent to Ramsden issued Jan. 16, 1973 as U.S. Pat. No. 3,711,560, the production of polyolefins and other oxygenated organic compounds which are polyunsaturated is discussed.

In U.S. Pat. No. 3,787,459 issued Jan. 22, 1974 to Frankel a process is described for converting unsaturated vegetable oil into formyl products which are subsequently reduced to the corresponding hydroxymethyl derivative or oxidized to the corresponding carboxy products. U.S. Pat. No. 3,899,442 issued Aug. 12, 1975 to Friedrich discusses a complementary system to that of the Frankel patent whereby rhodium catalysts are recovered from the spent hydroformylation reactants. Frankel, again in U.S. Pat. No. 3,928,231, issued Dec. 23, 1975 discusses a process of preparing carboxy acid products in high yields while minimizing isomerization of the starting unsaturated vegetable oil. Miller et al in U.S. Pat. No. 4,093,637 issued June 6, 1978 discusses the use of formyl stearic acid to prepare bis acyloxymethyl-stearic acid which is stated to be useful as a plasticizer.

U.S. Pat. No. 3,931,332 issued Jan. 6, 1976 to Wilkes discusses hydroformylation reactions in which the destructive disassociation of the catalyst is inhibited by the presence of organic nitrogen compounds. Reichspatentamt Patentschrift No. 745,265 to Mannes et al published Mar. 1, 1944 discusses the preparation of dicarboxylic acids and their salts. In Bundesrepublik Deutschland Pat. No. 965 697 issued June 13, 1957 to Blaser and Stein the reaction of unsaturated alcohols and their derivatives with metal carbonyls and carbon monoxide is discussed. A by-product which is obtained through the technology of Blaser et al includes substantial amounts of monoformylated product. Similarly a formylation technique which results in a monoformylated product when using unsaturated alcohols is discussed in an article by Ucciani et al in the Bull. Soc. Chim. (France) 1969 p. 2826–2830. Similarly Bundesrepublik Pat. No. 1,054,444 published Apr. 9, 1959 to Waldmann and Stein discusses the treatment of unsaturated fatty substances with formaldehyde in the presence of a carboxylic anhydride and an acidic catalyst to provide formyl products.

Substantial work has been done on the production of various hydroformylated products by the United States Department of Agriculture at its Regional Research Laboratories. For example, in an article by Roe entitled "Branched Carboxylic Acids from Long-Chain Unsaturated Compounds and Carbon Monoxide at Atmospheric Pressure" published at J. Am. Oil Chemists' Soc. 37, p. 661–668 (1960). The production by direct carboxylation at atmospheric pressure of unsaturated acids with carbon monoxide or formic acid is discussed. Polyols from hydroformylation are described in an article entitled "Preparation of 2-Decyl-2-Hydroxymethyl-1,3-Propanediol from Dodecanol and Petroselinic Acid" by Holmes et al at J. Am. Oil Chemists' Soc. 42, No. 10, pages 833–835 (1965). The hydroformylation of unsaturated fatty esters is discussed by Frankel et al at J. Am. Oil Chemists' Soc. 46, p. 133–138 (1968). Frankel has also reported a selective catalyst system for the hydroformylation of methyl oleate utilizing rhodium catalyst in the presence of triphenylphosphine in an article entitled "Methyl 9 (10)-Formylstearate by Selective Hydroformylation of Oleic Oils" at J. Am Oil Chemists' Soc. 48, p. 248–253 (1971).

In a paper presented at the American Oil Chemists' Society meeting in Atlantic City, New Jersey in 1971, Dufek et al discusses the esterification and transesterification of dicarboxylic acids under the title "Esterification and Transesterification of 9 (10)-Carboxystearic Acid and Its Methyl Esters". The foregoing article was published at J. Am. Oil Chemists' Soc. 49 (5) p. 302–306 (1972). Frankel, again, discusses the use of specific catalysts to obtain hydroformylated products in an article titled "Selective Hydroformylation of Polyunsaturated Fats With a Rhodium-Triphenylphosphine Catalyst", J. Am. Oil Chemists' Soc. 49, p. 10–14 (1972). Friedrich at Vol. 17, No. 3 of Ind. Eng. Chem. Prod. Res. Dev. (1978) presents an article entitled "Low-Pressure Hydroformylation of Methyl-Oleate With an Activated Rhodium Catalyst".

Pryde, working with Frankel and Cowan discuss hydroformylation via the oxo reaction, Koch carboxylation and Reppe carbonylation in an article entitled "Reactions of Carbon Monoxide with Unsaturated Fatty Acids and Derivatives: A Review", reported at J. Am. Oil Chemists' Soc. 49, p. 451–456 (1972).

Friedrich discusses the hydroformylation of unsaturated esters combined with catalyst recovery in an article entitled "Hydroformylation of Methyl Oleate with a Recycled Rhodium Catalyst and Estimated Costs for a Batch Process" at J. Am. Oil Chemists' Soc. 50, p. 455–458 (1973). A similar area of technology is also reported by Frankel et al in an article entitled "Hydroformylation of Methyl Linoleate and Linolenate with Rhodium-Triphenylphosphine Catalyst" from I&EC Product Research & Development, Vol. 12, p. 47–53 (1973).

Certain condensation polymers prepared from pentaerythritol acetal derivatives are reported in an article "Poly(Amide-Acetals) and Poly(Ester-Acetals) from Polyol Acetals of Methyl (9(10)-Formylstearate: Preparation and Physical Characterization" reported at J. Am. Oil Chemists' Soc. 53, p. 20–26 (1976). Compounds obtained through hydroformylation technology useful as plasticizers are discussed in a Frankel et al article entitled "Acyl Esters from Oxo-Derived Hydroxymethylstearates as Plasticizers for Polyvinyl Chloride" printed in the J. Am. Oil Chemists' Soc. 52, p. 498–504 (1975).

Friedrich in an article entitled "Oxidation of Methyl Formylstearate with Molecular Oxygen" at J. Am. Oil Chemists' Soc. 53, p. 125–129 (1976) reports the use of air or oxygen to form methyl carboxystearate from methyl formylstearate in an emulsion with a soluble rhodium complex. The reuse of catalyst in hydroformylation reactions is described by Awl in an article entitled "Hydroformylation with Recycled Rhodium Catalyst and One-Step Esterification-Acetalation: A Process for Methyl 9(10)-Methoxymethylenestearate from Oleic Acid" which is printed in J. Am. Oil Chemists' Soc. 53, p. 190–195 (1976).

Useful diols for resin purposes are described in U.S. Pat. No. 2,933,477 issued Apr. 19, 1960 to Hostettler. Nonadecanediols are described as being utilized in urethane formulations in U.S. Pat. No. 3,243,414 to DeWitt et al issued Mar. 29, 1966. The production of triols which are not particularily useful in resins due to the close positioning of the hydroxyl groups is reported in Improved Synthesis of 1,1,1-trimethylolalkanes from Hexanal and Nonanal J. Am. Oil Chemists' Soc. 45, p. 517 (July 1968) by Moore and Pryde. Polyols similar to those described by Moore et al are disclosed in British Pat. No. 867,230 published May 3, 1961.

Frankel et al in a paper entitled Catalytic Hydroformylation and Hydrocarboxylation of Unsaturated Fatty Compounds at J. Am. Oil Chemists' Soc. 54, p. 873A (1977) also describes formylation technology. Frankel also describes the use of carbonyl metallic compounds in hydroformylations in an article entitled "Catalytic Hydroformylation of UnSaturated Fatty Derivatives with Cobalt Carbonyl" by J. Am. Oil Chemists' Soc. 53, p. 138–141 (1976). The use of esters of various carboxystearic acids is discussed by Dufek et al in an article entitled "Some Esters of Mono-, Di-, and Tricarboxystearic Acid as Plasticizers: Preparation and Evaluation" at J. Am. Oil Chemists' Soc. 53, p. 198–203 (1976).

Dufek et al also report catalyst recovery in an article entitled "Recovery of Solubilized Rhodium from Hydroformylated Vegetable Oils and Their Methyl Esters" in J. Am. Oil Chemists' Soc. 54, p. 276–278.

Frankel discusses hydroformylation generally in an article entitled Selective Hydroformylation of Unsaturated Fatty Acid Esters at Annals N.Y. Academy of Sciences 214:79 (1973). Catalyst technology is reviewed at Recent Developments in Hydroformylation Catalysis in Catal. Rev. 6 (1) page 49 et seq. (1972).

Dufek alone at J. Am. Oil Chemists' Soc. 55, p. 337–339 (1978) reports on the conversion of methyl 9(10) formylstearate in an article entitled "Conversion of Methyl 9(10)-Formylstearate to Carboxymethylstearate".

Acetal esters obtainable through hydroformylation technology are reported by Adlof et al in an article entitled "Preparation and Selective Hydrolysis of Acetal Esters" at J. Am. Oil Chemists' Soc. 54, p. 414–416 (1977). Selective catalyst systems are again reported by Frankel in the J. Am. Oil Chemists' Soc. 54, p. 873a–881a (1977) in an article entitled "Catalytic Hydroformylation and Hydrocarboxylation of Unsaturated Fatty Compounds".

The plasticization of polyvinylchloride resins is also reported in patent applications coded P.C. 6333 and 6375 bearing respectively the titles "Acetoxymethyl Derivatives of Polyunsaturated Fatty Triglycerides as Primary Plasticizers for Polyvinylchloride", and "Alkyl 9,9(10,10)-Bis(acyloxymethyl) octadecanoates as Primary Plasticizers for Polyvinylchloride". P.C. 6333 issued as U.S. Pat. No. 4,083,816 on Apr. 11, 1978. P.C. 6375 issued as U.S. Pat. No. 4,093,637 on June 6, 1978.

Each of the foregoing to the extent that it is applicable to the present invention is herein incorporated by reference.

The basic purpose of the present invention is to describe as end products the polyglycidyl ethers of high molecular weight polyhydric alcohols. These polyglycidyl ethers are highly useful as curing agents for amines and amides in the coating arts. Of course several other uses of the technology embodied in this patent are readily apparent.

Throughout the specification and claims of the present invention percentages and ratios are by weight and temperatures are in degrees of Celsius unless otherwise indicated. The terms polyglycidyl ether and oxirane or epoxy of the high molecular weight polyhydric alcohols are used synonymously.

SUMMARY OF THE INVENTION

The present invention is a composition of matter comprising a polyglycidyl ether of a polyol selected from the group consisting of:

$$H(CH_2)_h CH(CH_2OH)(CH_2)_k CH_2OH \qquad (a)$$

and $$CH_3(CH_2)_m[C(CH_2OH)_2]_n(CH_2)_p[C(CH_2OH)_2]_q(CH_2)_r[C(CH_2OH)_2]_s(CH_2)_t CH_2OH \qquad (b)$$

and mixtures thereof
wherein n plus q plus s are integers the sum of which is from 1 to 3; k and t are 3 or greater; n, q, and s are 0 or 1; m through t are integers the sum of which is from 12 to 20; and, h plus k are non-zero integers the sum of which is from 12 to 20.

DETAILED DESCRIPTION OF THE INVENTION

The polyglycidyl ethers of the present invention are obtained from alcohols which are obtained in turn by hydroformylation processes. Hydroformylation is the process for the production of aldehydes from olefinically unsaturated compounds by reaction with carbon monoxide and hydrogen in the presence of a catalyst. The aldehydes produced generally correspond to the compounds obtained by the addition of a hydrogen and a formyl group to an olefinically unsaturated group in the starting material thus saturating the olefinic bond.

The useful products of the present invention are prepared by hydroformylating an unsaturated alcohol of the formula $$H(CH_2)_a(CH=CH)_b(CH_2)_c(CH=CH)_d(CH_2)_e(CH=CH)_f(CH_2)_gCH_2OH$$

where hereinafter (1) a and g are not equal to 0; (2) the integers b plus d plus f are equal to y which has a value of from 1 to 3; (3) the sum of the integers a plus c plus e plus g is equal to x; and (4) x plus 2y is equal to from 13 to 21.

In the polyglycidyl ether (5) m through t are integers the sum of which is from 12 through 20; (6) n plus q plus s are 1 through 3; and; (7) n, q, and s are 0 or 1, preferably such that the sum of m through t is from 14 to 18 and x plus 2y is 15 to 19; and (8) k and t are each 3 or greater. It is particularly preferred that h plus k are non-zero integers the sum of which is from 12 to 20, preferably 14 to 18 and where h, m, k and t each are 4, 5 or 6 or greater. It is also preferred that n and s are 0 and q is 1. Most preferably the starting raw material is oleyl alcohol although linoleyl or linolenyl alcohol may be employed. It is, of course, noted that any number of synthetic unsaturated alcohols may also be employed in the present invention. However, for most purposes the naturally occurring alcohols derived from plant sources are presently most convenient and inexpensive.

The unsaturated alcohol is reacted with hydrogen gas and carbon monoxide in the presence of a rhodium catalyst as later described to form the corresponding formyl alcohol having the formula $$CH_3(CH_2)_m[CH(CHO)]_n(CH_2)_p[CH(CHO)]_q(CH_2)_r[CH(CHO)]_s(CH_2)_tCH_2OH$$

wherein the various subscript numbers are as previously described.

The addition of hydrogen and carbon monoxide is accomplished in practice by conveniently adding stoichiometric amounts of the hydrogen and carbon monoxide to give the formyl alcohol. To assure completeness of the reaction the amounts of hydrogen and carbon monoxide may be each maintained at from about 1.5:0.5 to about 0.5:1.5 molar ratio to one another. It is noted that the ratio is not critical as long as the pressure is maintained in the reaction vessel by the component gases and that the amount of hydrogen is not so great as to substantially reduce the unsaturated starting material.

The rhodium catalyst as later described is necessary in the hydroformylation reaction in that it has been found that the use of the more conventional cobalt catalyst results in a substantial amount of cross-linking gelation. It is believed that the gelation is due to the coproduction of polyhemiacetals and polyacetals in competition with the production of the hydroformylated alcohol. It was at first believed by the author that it would be necessary, even with a rhodium catalyst, to employ the ester of the unsaturated alcohol e.g. oleyl acetate to avoid the unwanted by-products. Of course, the ester is more expensive and eventually is converted to the alcohol in any event.

Higher yields of product are obtained through the use of the rhodium catalysts than if a cobalt catalyst is employed. It has also been observed that a much higher degree of isomerization of the double bond occurs with a cobalt catalyst than with a rhodium catalyst.

The conditions for pressure and temperature during the hydroformylation are conveniently conducted at from about 90 degrees C. to about 170 degrees C., preferably from about 110 degrees C. to about 130 degrees C. Above the higher temperatures listed above increased amounts of unwanted by-products are formed in the reaction mixture. The pressure conditions are such that the pressure in the sealed system is maintained at from about 20 to about 500 atmospheres, preferably from about 30 to about 100 atmospheres absolute during the hydroformylation.

The preferred end product obtained from conducting the foregoing process is 9(10) formyl octadecanol when the starting material is oleyl alcohol. The positioning of the 9(10) indicates that the product obtained is a mixture of the 9 and 10 isomer with respect to the formyl group. One additional reason for using a rhodium catalyst is that if a cobalt catalyst were employed a considerable amount of terminal aldehyde would be formed due to bond migration prior to the addition of the formyl group. When the terminal aldehyde group is formed the resultant alcohol obtained by carrying out the remainder of the process is unsuitable for many of the purposes that the desired alcohols may be utilized. That is, it has been found that terminal aldehydes are high melting thus resulting in solid polyglycidyl ethers which require solvents and/or high temperatures for use as curing agents.

It should also be appreciated that if 9,12-linoleyl alcohol is the starting material then the formyl alcohol so formed will be a 9(10), 12(13) diformyloctadecanol. That is, the end product obtained here will actually be a mixture of the 9-12,9-13,10-12,10-13 diformyl alcohol. Similarly, without discussing all the particular isomers present when 9,12,15-linolenyl alcohol is employed the product so obtained will be a mixture of the 9(10),12(13),15(16) triformyloctadecanol isomers.

It is particularly important that the expensive rhodium catalyst is recovered. This may be conveniently done by distillation of the formyl alcohol leaving the rhodium in the residue. What is particularly surprising is that the rhodium can be recovered from the distillate in that the art would predict that when hydroformylating an unsaturated alcohol that the products obtained would include considerable quantities of polyhemiacetals and polyacetals as a portion or all of the reaction product and that these products would not be recoverable by distillation. Thus, not only is the desired end product achieved in a high degree of purity and yield through the use of the rhodium catalyst but the rhodium catalyst is recoverable in extremely high quantities from the reaction mixture.

It should also be emphasized that if the polyhemiacetals and polyketals were formed in the reaction mixture that it is very likely that the reaction components would undergo a great change in viscosity to the point of forming a semi-solid product due to the extensive cross-linking of the acetal and ketal linkages. Thus a substantial reason exists for avoiding the polyhemiacetal and polyacetal formation through the use of a rhodium catalyst.

It may be stated that the polyacetal and polyhemiacetal formation might be prevented by the utilization of the corresponding unsaturated acid or its ester in place of the unsaturated alcohol. However, this substitution which eventually involves the acid ester is undesirable in that an aqueous neutralization step is required which forms a soap as a by-product. The soap so formed then emulsifies the reaction products and the water present to make separation extremely difficult thus diminishing recovery of both the alcohol and the expensive catalyst. Thus, the present invention is highly selective to both the unsaturated alcohol and the particular rhodium catalyst so employed.

Any convenient source of rhodium may be employed as in the present reaction mixture the rhodium catalyst is actually converted through the presence of the hydrogen and carbon monoxide into its active form which is a rhodium carbonyl hydride. Conveniently, the source of rhodium for use in the rhodium catalyst may be rhodium metal, rhodium oxide, and various other rhodium salts such as rhodium chloride, rhodium dicarbonyl chloride dimer, rhodium nitrate, rhodium trichloride and other similar materials.

The rhodium catalyst in the present hydroformylation reaction is preferably present with a ligand such as a trisubstituted phosphine or trisubstituted phosphite. The term trisubstituted includes both alkyl and aryl compounds and the substituted compounds of the alkyl and aryl compounds. A particularly valuable ligand for the rhodium carbonyl hydride is a triphenylphosphite or triphenylphosphine in that both compounds are particularly useful in minimizing migration of the double bond thereby avoiding a large number of isomers with respect to the formyl group including the undesired terminal formyl compound as previously discussed. In general triaryl phosphines or triarylphosphites may be used for this purpose in the formation of the rhodium carbonyl hydride ligand. In addition, the foregoing materials are extremely valuable in minimizing the undesired reaction of saturation of the double bond or the reduction formyl group. This frequently occurs in the absence of such ligands because the rhodium catalyst functions excellently as a hydrogenation catalyst. That is the ligand tends to eliminate such side reactions.

In general anyone of several other additional ligands may be used with the rhodium catalyst. Such additional ligands are discussed in the Selective Hydroformylation of Unsaturated Fatty Acid Esters by Frankel in the Annals N.Y. Academy of Sciences 214:79 (1973).

The various ligands are conveniently employed in mole ratio to the rhodium metal content of the catalyst of from about 2 to 50 preferably from 3 to 20. The rhodium catalyst based upon its metal content is conveniently employed in catalytic amounts preferably from about 20 ppm to about 10,000 ppm, most preferably from about 50 ppm to about 500 ppm by weight of the unsaturated alcohol.

The various formyl alcohols are useful as previously stated in preparing the highly desired gem-bis(hydroxymethyl) alcohols. The alcohols may be formed from the foregoing formyl alcohols via a Tollens' reaction (aldol condensation followed by a crossed-Cannizzaro reaction).

Schematically the Tollens' reaction is as described below.

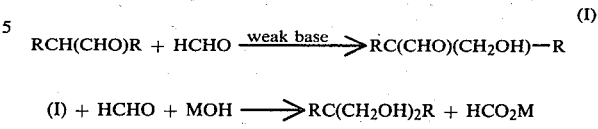

$$RCH(CHO)R + HCHO \xrightarrow{\text{weak base}} RC(CHO)(CH_2OH)-R \quad (I)$$

$$(I) + HCHO + MOH \longrightarrow RC(CH_2OH)_2R + HCO_2M$$

wherein the above formula R indicates an organic moiety, compound (I) is a hydroxymethyl aldehyde and MOH is a strong base.

The Tollens' reaction is thus carried out by reacting one mole of a monoformylated alcohol with two moles of formaldehyde in an inert atmosphere such as nitrogen. Where the formyl alcohol contains more than one formyl group, two moles of formaldehyde are required for each formyl group present. Thus, if the reactant is formyloctadecanol then two moles of formaldehyde are required for conversion to the gem-bis(hydroxymethyl) alcohol whereas if linoleyl alcohol is utilized in the first instance to give a diformyloctadecanol then four moles of formaldehyde are required to obtain the digeminaloctadecanol. Conveniently an excess of up to 1.5, preferably up to 1.2 times the amount of formaldehyde actually required to form the corresponding gem-bis(hydroxymethyl) alcohol is employed in the present invention. A convenient manner of adding the formaldehyde in the Tollens' reaction is by using a methanol solution of formaldehyde.

The Tollens' reaction utilizes a strong base as both a reactant and a catalyst. Such strong bases include sodium, potassium or calcium hydroxide. Other strong bases such as carbonates or other hydroxides may be used as well. The strong base is conveniently employed on an equivalent basis per formyl group to convert the formyl group to the hydroxy methyl group. The amount of base required in the Tollens' reaction is at least an equivalent of that required preferably up to 1.5, most preferably up to 1.2 equivalents. The Tollens' reaction is conducted at a temperature of from about 0 degrees C. to about 100 degrees C., preferably from about 20 degrees C. to about 70 degrees C.

The crude gem-bis(hydroxymethyl) alcohol so formed is washed with water to remove any excess caustic and salts formed and then obtained in a relatively pure state by vacuum drying.

In obtaining the gem-bis(hydroxymethyl) alcohol of the present invention the crossed-Cannizzaro reaction predominates over the rate of reaction for the simple Cannizzaro reaction.

The Cannizzaro reaction which is promoted by base, water, and heat is the process by which an aldehyde reacts with itself to form the corresponding alcohol and formate salt. That is, in the present invention the formyl group on the formyl alcohol reacts faster with formaldehyde to give the alcohol than does the formaldehyde react with itself despite the steric hinderance of the larger formyl alcohol molecule.

It is also surprising that the formation of hemiacetal which may be acid or base catalyzed does not occur upon the addition of base to the formyl alcohol while forming the intermediate hydroxymethyl formyl alcohol. Thus two potential side reactions, the Cannizzaro and the hemiacetal formation (and thereafter the acetal) which might be expected given the reactants and the processing conditions involved do not in fact occur and the useful alcohol is obtained in substantial quantities.

An alternative method of accomplishing the formation of the geminal alcohol is to use only about one-half the equivalent amount of the formaldehyde required in the Tollens' reaction thereby forming the corresponding hydroxymethyl formyl alcohol via the aldol condensation. That is, the hydroxymethyl group is attached to the carbon in the alpha position to the formyl group. Where a polyformyl alcohol is the intermediate product the formaldehyde is halved from that utilized in the Tollens' reaction to give the corresponding polyhydroxymethyl polyformyl alcohol.

This variation of forming the geminal alcohol eliminates the need for the strong base required in the Tollens' reaction and utilizes instead only catalytic amounts of base which may be either a weak or strong base. A preferred weak base is triethylamine. Even here some care must be taken as it is possible even when using a weak base to obtain compound (I) as the Cannizzaro reaction may compete with the aldol condensation.

The hydroxymethyl formyl alcohol so formed by this alternative route is then reduced to the alcohol conveniently by using hydrogen gas and a suitable hydrogenation catalyst such as copper chromite, or nickel, via conventional hydrogenation practice or by lithium aluminum hydride production. A significant advantage to the alternative route is the absence of large amounts of salt and solvents needed in the Tollens' reaction route.

A distinct advantage in the geminal alcohol of the present invention is that it is a liquid at room temperature and further has no tertiary hydrogens which are a weak point for chemical attack on the molecule.

A mixture of the diol and the geminal alcohol is obtained by reacting the unsaturated alcohol to obtain the corresponding formyl alcohol. Thereafter the formyl alcohol is split into two streams, the first of which is processed as previously discussed to give the geminal alcohol while the second stream is reduced by hydrogenation to give the diol. The hydrogenation is generally carried out as discussed in the alterative route for preparing the geminal alcohol. The diol and the geminal alcohol are then recombined in the desired proportions which are preferably in a weight ratio of from about 2:1 to about 1:100 more preferably from about 1:1 to about 1:75. The liquid nature of the geminal alcohol aids in solubilizing the normally solid diol thus giving a product which is easy to compound into the corresponding polyglycidyl ether.

The polyglycidyl ethers of the present invention may be prepared according to the general technology disclosed in U.S. Pat. No. 4,110,354 issued Aug. 29, 1978 to Bertram et al which is herein incorporated by reference. More specifically, the polyglycidyl ethers of the present invention are prepared by reacting equivalent amounts of epichlorohydrin to the starting alcohol. It is preferred that the epichlorohydrin be added slowly to the starting alcohol in the presence of an acid such as boron trifluoride, tin tetrachloride, hydrofluoric acid or sulfuric acid to fully achieve the desired reaction product. It is, however, possible to form higher polyglycidyl ethers due to the fact that some of the epichlorohydrin will add to the starting alcohol in a fashion such that another primary alcohol is produced which then may react with a second mole of epichlorohydrin prior to the closing of the oxirane structure through the use of the base. Thus, chlorinated byproducts are thereby obtained. In the oxirane formation itself water and sodium chloride are liberated when sodium hydroxide is utilized as the source of strong base. It is possible, however, to use other strong bases such as potassium hydroxide or calcium hydroxide depending upon the reaction conditions and the tolerance for impurities in the reaction mixture. The amount of the strong base employed is simply an equivalent amount as required in the reaction. The product may also be formed through addition of the corresponding allyl ether followed by oxidation to the oxirane.

The reaction to form the polyglycidyl ether is conveniently conducted in dichloroethane although solvents such as toluene may also be employed. Following the closing of the epichlorohydrin structure to give the oxirane or polyglycidyl ether, the water so formed may be azeotropically distilled from the reaction mixture.

For the purposes of forming a fully cross-linked coating it is desirable that the polyglycidyl ether contain 1.5 oxirane units or greater per starting molecule of the alcohol. The figure, of course, is only an average of that required and a normal distribution will be found depending upon the particular reaction conditions employed. Most preferably the product should contain two or greater oxirane units per mole of the starting diol alcohol, most preferably 3 for the higher polyols.

The addition of the epichlorohydrin should be conducted at as low a temperature as is reasonably possible to minimize the amount of polyglycidyl ether polymers formed. Desirably this temperature is kept between about 10 degrees C. and 50 degrees C., preferably from about 20 degrees C. to about 25 degrees C. However, the reaction mixture upon full addition of the epichlorohydrin in a dropwise fashion is preferably maintained at from about 40 degrees C. to about 100 degrees C., most preferably from about 60 degrees C. to about 80 degrees C. during a period of from about 10 minutes to two hours preferably about 1 hour to ensure a complete reaction of the components.

The products of the present invention are useful as curing agents for amines, amides, anhydrides, acids, mercaptans and the like. Suggested uses of epoxy coatings are found in the publication of Federation Series on Coatings Technology, Unit 20, Epoxy Resins in Coatings, published by the Federation of Societies For Paint Technology, by Roy Al Allen, Copyrighted 1972.

The polyglycidyl ethers of the present invention have been found to be extremely light stable due to the absence of any aromatic structure or methylidyne hydrogens in the geminal polyglycidyl ethers. The non geminal polyglycidyl ethers of the present invention still enjoy the stability of the absence of aromatic rings.

The products of the present invention give epoxy cured coatings which are found to have high gloss, great light stability and the absence of chalking upon atmospheric weathering. The polyglycidyl ethers are observed to have extremely low viscosity and therefore are highly suitable as reactive diluents for other higher molecular weight epoxies which must otherwise be thinned with solvents. It is possible through the technology of the present application to form a 100% solids coating with the geminal polyglycidyl ethers of the present invention.

The following are examples of the present invention:

EXAMPLE I

The manufacture of the formyloctadecanol precursor is accomplished by charging a 1 liter Magne Drive, 316 SS autoclave with 606 grams (2.26 moles) of oleyl alcohol, 3.01 grams of 5% rhodium on alumina and 3 grams (9.68 moles) of triphenylphosphite.

The autoclave is sealed and pressurized to 10 atmospheres with nitrogen under stirring and then vented to atmospheric pressure. The nitrogen purge is repeated twice more to ensure removal of any oxygen present in the autoclave.

The autoclave is then pressurized a third time with premixed carbon monoxide and hydrogen gas in a 1 to 1 molar ratio to 68 atmospheres at which point heating is started. Stirring is manually controlled at 1250 rpm and the uptake of the mixture of the gases starts at about 100 degrees C. The reaction conditions are then maintained at a temperature of 130 degrees C. and the gas pressure at 70 to 75 atmospheres.

The reaction is substantially complete after 4.6 hours and is determined by the cessation of the gas uptake. The confirmation of completeness of the reaction is obtained by sampling the mixture and determining through gas chromatograph analysis that there is less than 1% of the starting alcohol in the mixture.

The reaction mixture is then cooled to 75 degrees C., vented to atmospheric pressure and purged twice with nitrogen. The contents of the autoclave are then discharged at 75 degrees C. under nitrogen pressure through a pressure filter. The yield of the formyloctadecanol is greater than 90%. Atomic absorption analysis of the filtered product showed 244 ppm of rhodium.

The reaction may be modified by using triphenylphosphine in place of the triphenylphosphite. Alternatively, the oleyl alcohol may be substituted for by linoleyl or linolenyl alcohol. The reaction temperature may also be lowered to 90 degrees C. at which point the reaction takes a substantially longer period of time to proceed. As a second alternative, the reaction temperature can be raised to about 170 degrees C. and the reaction time considerably lowered. However, some decomposition of the end product may occur above the 170 degree figure so it should not be exceeded.

In similar fashion the mixture of carbon monoxide and hydrogen may be varied as previously described in the Detailed Description of the Invention and may also be varied between about 20 and 500 atmospheres of pressure. The lower end of the pressure range of course, slows the reaction rate down while the higher pressure condition increases the reaction but also increases the probability that some of the starting alcohol will be saturated by the hydrogen.

EXAMPLE II 5.26 moles (1570 grams) of the formyloctadecanol obtained from Example I is charged into a 5 liter glass round bottom reaction flask equipped with a heat exchanger coil, thermocouple, stirrer, addition inlet, reflux condensor and combination glass electrode. A further reaction charge of 695 grams (12.87 moles) of a 55.6% formaldehyde in methanol solution is added under a nitrogen blanket. A 40% solution of sodium hydroxide is made by dissolving 245.7 grams (5.95 moles) of sodium hydroxide in 368 grams of water under a nitrogen blanket. The caustic solution is added to a charge tank and connected to the feed side of a metering pump.

The reaction mixture is heated to 30 degrees C. and the caustic carefully added by means of a metering pump with stirring to adjust the pH to about 10.9. After about forty minutes at 30 degrees C. the addition of the 40% caustic solution is started at a rate of 9.65 milliliters per minute and the temperature of the reaction is increased to 60 degrees C. The addition of caustic required about 45 minutes and the reaction temperature was maintained at 60 degrees C. Gas chromatograph analysis of a sample taken at this time indicated that the reaction was complete and that the gem-bis(hydroxymethyl) alcohol corresponding to the formyloctadecanol is formed.

The reaction is held for an additional 20 minutes at 60 degrees C. after completion of the caustic addition. The stirring is then stopped and the lower aqueous phase (816 grams) was allowed to separate.

After washing of the crude gem-bis(hydroxymethyl) octadecanol and its drying under vacuum the amount recovered is 1711 grams corresponding to a yield of greater than 90%.

Alternatively linoleyl or linolenyl alcohol derivatives of Example I may be employed under similar conditions. The reaction temperature for the production of the bishydroxymethyloctadecanol is to use 6.43 moles of the 55.6% formaldehyde solution thereby yielding the corresponding hydroxymethyl formyloctadecanol as an isolatable product. This material is then reduced through catalytic hydrogenation with copper chromite or through the use of lithium aluminum hydride to give the gem-bis(hydroxymethyl)-octadecanol.

An alternative method of obtaining the bishydroxymethyloctadecanol is to use 6.43 moles of the 55.6% formaldehyde solution thereby yielding the corresponding hydroxymethyl formyloctadecanol as an isolatable product. This material is then reduced through catalytic hydrogenation with copper chromite or through the use of lithium aluminum hydride to give the gem-bis(hydroxymethyl)octadecanol.

EXAMPLE III

The formyl alcohol of Example I is divided into separate streams and one part is converted to the gem-bis(hydroxymethyl) alcohol of Example II. The second stream is hydrogenated by charging 1928 grams (6.46 moles) of the formyloctadecanol and a slurry of 108 grams of water-wet Raney nickel which has been washed twice with two 100 ml portions of ethanol.

The autoclave (316 SS) is sealed and pressurized to 10 atmospheres of nitrogen with stirring. The autoclave is then vented and then purged twice more with nitrogen to ensure that the oxygen is substantially removed.

The autoclave is then pressurized to 55 atmospheres with hydrogen and stirring is commenced. The temperature is controlled between about 100 degrees C. and 116 degrees C. with the hydrogen uptake complete to give the 9(10)-hydroxymethyloctadecanol (diol) in about 2 hours at a yield of greater than 90%.

The diol is then mixed with the gem-bis(hydroxymethyl) alcohol in the desired proportions to give a liquid product.

EXAMPLE IV

The polyglycidyl ether of bis-hydroxymethyloctadecanol is formed as follows:

| INGREDIENTS | EQUIVALENTS | WEIGHT |
| --- | --- | --- |
| Bis-(hydroxymethyl)octadecanol | 1.00 | 114.7 |
| Epichlorohydrin | 1.00 | 92.5 |
| Toluene | — | 150.0 |
| $BF_3$ . etherate | .03 | 4.3 |

| INGREDIENTS | EQUIVALENTS | WEIGHT |
|---|---|---|
| NaOH (40% in water) | 1.00 | 100.0 |

Half of the volume of the toluene, the bis-hydroxymethyloctadecanol and the $BF_3$·etherate (borontrifluoride catalyst) are combined in a 1 liter round bottomed flask fitted with a stirrer, condenser, thermometer and ice bath. The epichlorohydrin is added dropwise over a period of one hour while the initial temperature is at 22 degrees C. and the exotherm is controlled with the ice bath. The reaction temperature is maintained at less than 25 degrees C. until all of the epichlorohydrin has been added and for an additional one hour.

The reaction mixture following the addition of the epichchlorohydrin is then heated to 70 degrees C. and held at that temperature for another hour.

The remaining toluene is then added to the reaction mixture and the mixture is heated to reflux temperature. A Dean Stark trap is added to the condenser and the sodium hydroxide is added over a period of one-half hour. During and after the addition, water is azeotropically distilled from the reaction mixture. A total of 77 milliliters of water (99% of the theoretical present) is collected.

Following this distillation, the reaction mixture is then cooled to about 30 degrees C. A large amount of sodium chloride and a waxy precipitate were observed to have been collected on the bottom of the flask. The solution is decanted and filtered through cheese cloth. Water and hydrochloric acid (0.1%) are added to neutralize the residual sodium hydroxide present in the mixture. More waxy precipitate is then seen at the interface and is removed.

The resultant polyglycidyl ether of the starting alcohol is then taken to 100% solids under vacuum.

Following the above example, the following additional parameters shown in Table I the various results shown are obtained.

TABLE I

| | | | | | | | | | | | |
|---|---|---|---|---|---|---|---|---|---|---|---|
| | | | | Bis-(hydroxymethyl)octadecanol | | | | | | | |
| RUN | SOLVENT | RATIO EPI/OH | TEMP. OF EPI ADDITION | EPI ADDITION TIME (MIN.) | TEMP NaOH ADDITION | NaOH ADDITION TIME (MIN.) | % TOTAL CHLORINE | SOLUTION VISCOSITY (P. 25° C.) | % SOLIDS | $O_x$ $O_2$ ON SOLIDS | GARDNER COLOR | EPOXY PER MOLECULE |
| A | Dichloroethane | 1/1 | 60 | 120 | 85 | 100 | | 1.7 | 96.7 | 6.9 | 1–2 | 2.0 |
| B | Toluene | 1/1 | 50 | 25 | 110 | 15 | 2.32 | 24.0 | 98.9 | 5.6 | 1–2 | 1.6 |
| C | Toluene | 1/1 | 20 | 50 | 110 | 25 | 2.60 | 32.0 | 100.0 | 5.6 | 2 | 1.6 |
| D | Toluene | 1/1.1 | 20 | 45 | 112 | 0 | 3.91 | 3.2 | 99.8 | 6.8 | 1–2 | 2.0 |

NOTES:
EPI indicates that the material added is epichlorohydrin.
EPI/OH ratio is the equivalent amount of each of the materials added.
% Total Chlorine is that found remaining in the product and no hydrolizable chlorine is measured.
Viscosity is shown in the column indicated by n.
% Solids is that amount obtained following vacuum applied to the recovered material.
The term $O_x O_2$ indicates oxirane oxygen on solids.
The Gardner Color is the standard test applied to mixtures and indicates that this material is nearly water white.
The Epoxy Per Molecule indicates the oxirane content per mole of alcohol.

TABLE II

| | | | | | Hydroxymethyl octadecanol | | | | | | | |
|---|---|---|---|---|---|---|---|---|---|---|---|---|
| RUN | SOLVENT | RATIO EPI/OH | TEMP. OF EPI ADDITION | EPI ADDITION TIME (MIN.) | TEMP NaOH ADDITION | NaOH ADDITION TIME (MIN.) | % TOTAL CHLORINE | SOLUTION VISCOSITY (P. 25° C.) | % SOLIDS | $O_x$ $O_2$ ON SOLIDS | GARDNER COLOR | EPOXY PER MOLECULE |
| E | Dichloroethane | 1.1 | 55 | 330 | 70 | 240 | — | — | 99.88 | 5.3 | — | 1.5 |

NOTES:
EPI indicates that the material added is epichlorohydrin.
EPI/OH ratio is the equivalent amount of each of the materials added.
% Total Chlorine is that found remaining in the product and no hydrolizable chlorine is measured.
Viscosity is shown in the column indicated by n.
% Solids is that amount obtained following vacuum applied to the recovered material.
The term $O_x O_2$ indicates oxirane oxygen on solids.
The Gardner Color is the standard test applied to mixtures and indicates that this material is nearly water white.
The Epoxy Per Molecule indicates the oxirane content per mole of alcohol.

EXAMPLE V

The polyglycidyl ether of the diol is formed as in Example IV utilizing equivalent weights of the various reactants. This material is found to be a low viscosity polyglycidyl ether containing more than 1.5 oxirane units per molecule on the average.

The alcohol employed in forming the polyglycidyl ether is that derived as the diol in Example III.

EXAMPLE VI

The polyglycidyl ether of Example IV and the polyglycidyl ether of Example V are separately cured utilizing diethylenetriamine.

An additional variation of this example is the curing of bisphenol A epoxide through use of mixtures containing from 10 to 90% by weight of the respective polyglycidyl ethers described above.

The above example may be further varied through curing the polyglycidyl ether with phthalic anhydride, phthalic acid, a polyaminoamide, a melamine or mercaptan.

What is claimed is:

1. The polyglycidyl ether of a polyol containing on the average more than 1.5 oxirane units per molecule wherein said polyol is selected from the group consisting of:

and mixtures thereof, wherein k is 3 or greater; and, h plus k are non-zero integers the sum of which is from 12 to 20.

2. The polyglycidyl ether of claim 1 wherein the sum of h plus k is from 14 to 18.

3. The polyglycidyl ether of claim 1 wherein one of h and k is 4 or greater.

4. The polyglycidyl ether of claim 1 wherein the starting alcohol is 9(10)-hydroxymethyloctadecanol.